United States Patent [19]

Herzig

[11] Patent Number: 5,466,845
[45] Date of Patent: Nov. 14, 1995

[54] SULFONIUM SALTS AND PROCESS FOR THEIR PREPARATION

[75] Inventor: Christian Herzig, Taching am See, Germany

[73] Assignee: Wacker-Chemie GmbH, Munich, Germany

[21] Appl. No.: 325,193

[22] PCT Filed: Jun. 12, 1992

§ 371 Date: PCT/EP93/01487

§ 371 Date: Oct. 20, 1994

§ 102(e) Date: Oct. 20, 1994

[87] PCT Pub. No.: WO93/25559

PCT Pub. Date: Dec. 23, 1993

[30] Foreign Application Priority Data

Jun. 12, 1992 [DE]  Germany ..................... 42 19 376.1

[51] Int. Cl.⁶ ................. C07F 9/66; C07F 9/90; C07F 19/00; C07F 7/02
[52] U.S. Cl. ................. 556/12; 556/28; 556/29; 556/64; 568/6; 568/13; 568/77; 549/62; 549/78; 549/214; 549/475; 549/497
[58] Field of Search .................. 556/64, 12, 28, 556/29; 568/5, 77, 13; 549/475, 497, 62, 78, 214

[56] References Cited

U.S. PATENT DOCUMENTS

| | | | |
|---|---|---|---|
| 4,161,478 | 7/1979 | Crivello | 260/327 B |
| 4,933,377 | 6/1990 | Saeva et al. | 522/31 |
| 4,980,492 | 12/1990 | Dektar et al. | 556/64 |
| 5,057,549 | 10/1991 | Herzig et al. | 522/99 |
| 5,113,006 | 5/1992 | Herzig | 556/453 |
| 5,159,088 | 10/1992 | Schwalm | 549/3 |
| 5,191,124 | 3/1993 | Schwalm et al. | 568/18 |
| 5,231,157 | 7/1993 | Herzig et al. | 528/15 |

FOREIGN PATENT DOCUMENTS

| | | |
|---|---|---|
| 0404031 | 12/1990 | European Pat. Off. . |
| 2518749 | 11/1975 | Germany . |
| 2839586 | 3/1979 | Germany . |
| 2518652 | 5/1983 | Germany . |
| 3935775 | 5/1991 | Germany . |
| 4002922 | 8/1991 | Germany . |
| 1518141 | 7/1978 | United Kingdom . |

OTHER PUBLICATIONS

Derwent Abstract 75–67345W/41 (1994).
Austral. J. Chem. 38, 1209 (1985), "Chlorosulfination of Aromatic Methyl Ethers with Thionyl Chloride" by K. H. Bell.

*Primary Examiner*—Porfirio Nazario-Gonzales
*Attorney, Agent, or Firm*—Martin Connaughton

[57] ABSTRACT

The present invention provides photoactive sulfonium salts which can be employed as photoinitiators for the polymerization of cationically polymerized organic substances and are soluble in these substances.

6 Claims, No Drawings

SULFONIUM SALTS AND PROCESS FOR THEIR PREPARATION

This application is a request for U.S. examination under 35 U.S.C. § 371 of International application No. PCT/EP93/01487, filed Jun. 11, 1993.

The invention relates to new sulfonium salts and to a process for their preparation.

Photoactive triarylsulfonium salts are disclosed in DE-A 25 18 749, DE-A 25 18 652 and DE-A 28 39 586 and are used as photoinitiators for the polymerization of cationically polymerizable organic substances, for example epoxides, vinyl ethers, organopolysiloxanes containing epoxy groups, organopolysiloxanes containing vinyloxy groups, and olefins. The cationically polymerizable substances are, however, nonpolar to slightly polar, especially when the polymerizable groups are present in organopolysiloxanes. EP-A 404 031 (published on Dec. 27, 1990, J. L. Desorcie et al., General Electric Company) describes triaryl sulfonium salts in which at least one aryl radical is substituted by a long-chain alkoxy group.

The object was to provide photoactive sulfonium salts which can be employed as photoinitiators for the polymerization of cationically polymerizable organic substances and which are soluble in these substances. The object is achieved by the invention.

The invention relates to sulfonium salts of the general formula

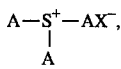

$$A-S^+-AX^-,$$
$$\quad\ |$$
$$\quad\ A$$

in which each A is identical or different and is a monovalent radical of the general formula

$$\begin{array}{c} E_b \\ | \\ -G-D_a \\ | \\ F_c \end{array}$$

in which

G is an aromatic hydrocarbon radical having 6 to 14 carbon atoms per radical or is an aromatic hydrocarbon radical having 5 to 14 ring atoms per radical which contains at least one oxygen and/or sulfur atom, with the proviso that one hydrogen atom in the radical G is replaced by a chemical bond to the sulfur atom, and D, E and F are each substituents of G, where D is a radical of the formula

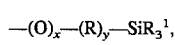

$$-(O)_x-(R)_y-SiR_3^1,$$

E is a radical of the formula

$$-OR^2,$$

F is a radical of the formula

$$-R^3,$$

a is 1, 2 or 3, b is 0, 1 or 2, c is 0, 1 or 2, x is 0 or 1, y is 0 or 1, preferably 1, R is a divalent hydrocarbon radical having 1 to 18 carbon atoms per radical, which is optionally interrupted by at least one oxygen atom and/or one sulfur atom and/or one carboxyl group, each $R^1$ is identical or different and is a monovalent hydrocarbon radical having 1 to 18 carbon atoms per radical, which is optionally interrupted by at least one oxygen atom, $R^2$ is a monovalent hydrocarbon radical having 1 to 18 carbon atoms per radical, which is optionally interrupted by at least one oxygen atom, $R^3$ is a monovalent hydrocarbon radical having 1 to 10 carbon atoms per radical, which is optionally interrupted by at least one oxygen atom and/or one sulfur atom, and $X^-$ is a halide ion $Z^-$ or a tosylate anion or a weakly nucleophilic or non-nucleophilic anion $Y^-$ selected from the group comprising $CF_3CO_2^-$, $BF_4^-$, $PF_6^-$, $AsF_6^-$, $SbF_6^-$, $ClO_4^-$, $HSO_4^-$ and $C_nF_{(2n+1-m)}H_m-SO_3^-$, in which n is an integer from 1 to 12 and m is 0 or an integer of up to 2n−1.

Examples of aromatic hydrocarbon radicals G are the phenyl, naphthyl and anthryl radicals.

Examples of aromatic hydrocarbon radicals G containing at least one oxygen and/or sulfur atom are the 2-furyl, 3-furyl, 2-thienyl and 3-thienyl radicals.

The radical A is preferably a radical of the formula

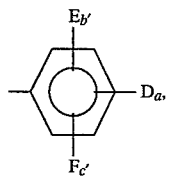

in which D, E and F are each a radical bonded in the 2-, 3-, 4-, 5- or 6-position on the benzene ring, D, E and F are as defined above and b' is 0 or 1 and c' is 0 or 1.

Examples of the divalent hydrocarbon radical R are $-CH_2-$, $-(CH_2)_2-$, $-(CH_2)_3-$, $-(CH_2)_4-$ and $-(CH_2)_6-$.

Examples of the divalent hydrocarbon radical R which is interrupted by at least one oxygen atom and/or sulfur atom and/or one carboxyl group are $-CH_2CH_2OCH_2CH_2-$, $-CH_2CH_2OCH_2CH_2CH_2-$ and $-CH_2CH_2OCH_2CH_2OCH_2CH_2CH_2-$.

Examples of hydrocarbon radicals $R^1$ are alkyl radicals such as the methyl, ethyl, n-propyl, isopropyl, n-butyl, isobutyl, tert-butyl, n-pentyl, isopentyl, neopentyl and tert-pentyl radical; hexyl radicals such as the n-hexyl radical; heptyl radicals such as the n-heptyl radical; octyl radicals such as the n-octyl radical, and isooctyl radicals such as the 2,2,4-trimethylpentyl radical; nonyl radicals such as the n-nonylradical; decyl radicals such as the n-decyl radical; dodecyl radicals such as the n-dodecyl radical and octadecyl radicals such as the n-octadecyl radical.

Examples of hydrocarbon radicals $R^1$ interrupted by at least one oxygen atom are alkoxyalkyl radicals such as $-CH_2CH_2OCH_3$, $-CH_2CH_2OCH_2CH_3$ and $-CH_2CH_2OCH_2CH_2CH_2CH_3$.

Preferably, all three radicals $R^1$ attached to the Si atom together contain from 3 to 25 aliphatic carbon atoms, preferably from 8 to 15 aliphatic carbon atoms.

The examples of radicals $R^1$ apply with full validity to the radicals $R^2$.

Examples of hydrocarbon radicals $R^3$ are alkyl radicals such as the methyl, ethyl, n-propyl, isopropyl, n-butyl, isobutyl, tert-butyl, n-pentyl, isopentyl, neopentyl and tert-pentyl radical; hexyl radicals such as the n-hexyl radical; heptyl radicals such as the n-heptyl radical; octyl radicals such as the n-octyl radical and isooctyl radicals such as the 2,2,4-trimethylpentyl radical; nonyl radicals such as the n-nonyl radical, and decyl radicals such as the n-decyl radical; aryl radicals such as the phenyl radical.

Examples of hydrocarbon radicals $R^3$ which are interrupted by at least one oxygen atom and/or sulfur atom are —$CH_2CH_2OCH_3$, —$CH_2CH_2OCH_2CH_3$ and —$CH_2CH_2SCH_2CH_3$.

Examples of radicals D are

—$O(CH_2)_3SiMe_2Et$

—$O(CH_2)_3SiMeBu_2$

—$O(CH_2)_3SiMeOct_2$

—$O(CH_2)_3SiBu_3$

—$O(CH_2)_2O(CH_2)_3SiMe_2Oct$

—$O(CH_2)_2O(CH_2)_3SiMeOct_2$

—$O(CH_2)_2O(CH_2)_3SiBu_3$

—$O(CH_2)_3SiEt_3$

—$(CH_2)_3SiMeOct_2$

—$(CH_2)_3SiMe_2Oct$ (in which Me is the methyl radical, Et is the ethyl radical, Bu is the n-butyl radical and Oct is the n-octyl radical), with the radicals —$O(CH_2)_2O(CH_2)_3SiMe_2Oct$ and —$(CH_2)_3SiMe_2Oct$ being preferred.

Examples of radicals E are the methoxy radical, ethoxy radical and n-butoxy radical.

Examples of radicals F are the methyl, ethyl, propyl, 2-methylpropyl and n-butyl radicals.

Examples of radicals A are

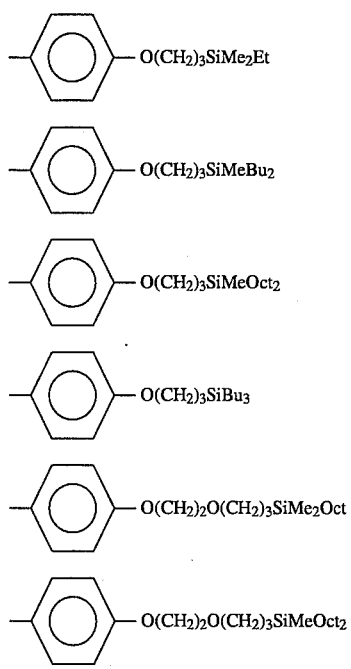

-continued

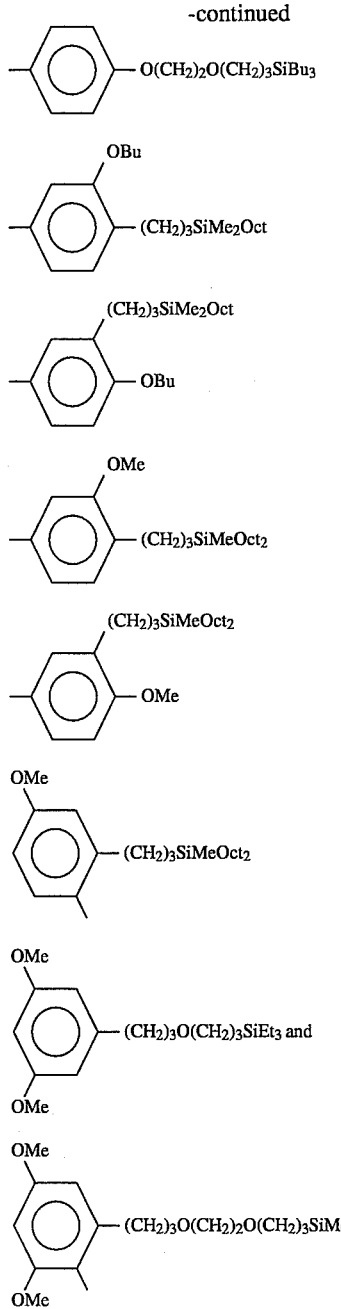

(in which Me is the methyl radical, Et is the ethyl radical, Bu is the n-butyl radical and Oct is the n-octyl radical).

Examples of the anion $C_nF_{(2n+1-m)}H_m$—$SO_3^-$ are the anions $CF_3SO_3^-$ and $C_4F_9SO_3^-$.

Preferred examples of anions $Y^-$ are $PF_6^-$, $AsF_6^-$ and $SbF_6^-$, with $SbF_6^-$ being particularly preferred.

Preferred sulfonium salts are those of the formula

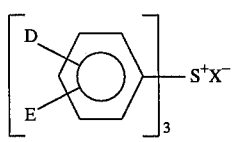

in which D, E and X are as defined above.

Particular preference is given to the sulfonium salt of the formula

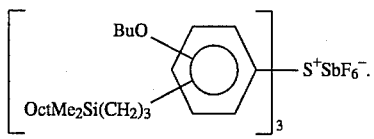

The solubility of the sulfonium salts according to the invention is significantly greater in nonpolar media such as n-alkanes than that of the comparable (same number of atoms in the substituent of the phenyl radical) sulfonium salts of EP-A 404 031 mentioned at the outset.

For example, the sulfonium salt of the formula

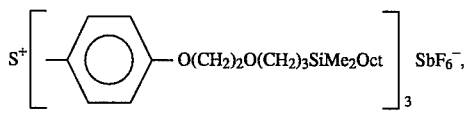

which contains 15 carbon atoms in the radical D, is of unlimited solubility in n-heptane.

The invention further relates to a process for the preparation of the sulfonium salts, which comprises in a 1st stage reacting a silane of the formula

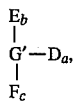

in which G' is an aromatic hydrocarbon radical having 6 to 14 carbon atoms per radical or an aromatic hydrocarbon radical having 5 to 14 ring atoms per radical and containing at least one oxygen and/or sulfur atom, and D, E and F are each substituents of G' and D, E, F, a, b and c are as defined above, with thionyl halide in the presence of a Lewis acid and an inert organic solvent to give a sulfonium halide of the formula

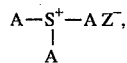

in which
Z⁻ is a halide ion and
A is as defined above, and optionally in a 2nd stage reacting the resulting sulfonium halide with an alkali metal salt of the formula

in which
M⁺ is an alkali metal cation, ammonium ion or quaternary ammonium cation and
Y⁻ is as defined above,
in the presence of organic solvent.

The radical G' is as defined for G with the proviso that the chemical bond to the sulfur atom in the radical G is replaced by a hydrogen atom.

Examples of silanes employed in the process according to the invention are

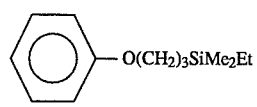

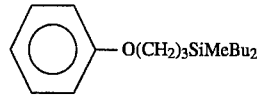

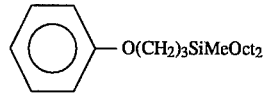

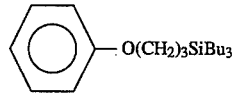

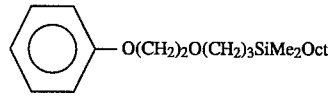

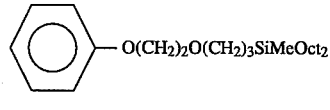

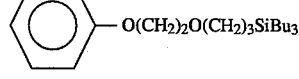

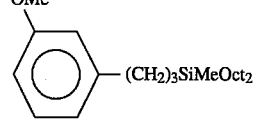

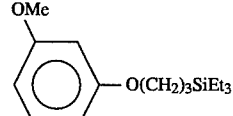

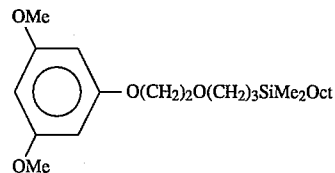

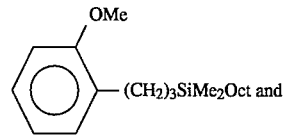

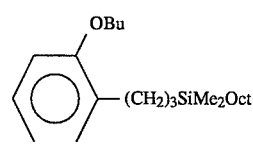

(in which Me is the methyl radical, Et is the ethyl radical, Bu is the n-butyl radical and Oct is the n-octyl radical).

The silanes employed in the process according to the invention, such as tetraalkylsilanes, can be prepared by known processes. They may, for example, be prepared as follows: phenyl allyl ether, obtainable by the method described in DE-A 39 35 775, is subjected to an addition reaction with hydridochlorosilanes in the presence of hydrosilylation catalysts, such as platinum catalysts, and the resulting phenoxyalkylchlorosilanes are alkylated using organometallic reagents, such as alkyllithium or alkyl Grignard compounds. Complete alkylation in this case requires an excess (from 10 to 50 mol %) of alkylmetal reagent, based on the chlorine atoms attached to Si. If not all the Si-attached chlorine atoms are exchanged for Si-attached alkyl groups, then this leads, during the working-up of the tetraalkylsilanes, to unwanted secondary reactions such as the formation of silanols or disiloxane formation.

The relatively long-chain silanes which are preferably employed, i.e. those having at least 15 aliphatic carbon atoms, are nondistillable oils which are in general highly fluid. Chemically they are substantially inert but possess, because of the phenyloxy group, a very good reactivity with respect to electrophiles.

The silanes are reacted with thionyl halide, with catalysis by Lewis acid, by the process of K. H. Bell, Austral. Journal of Chemistry 38, 1209 (1985). The process according to the invention is preferably carried out at a temperature of from 0° C. to 40° C. and preferably at the pressure of the surrounding atmosphere. If silanes containing at least two alkoxy groups attached to the aromatic structure, preferably to the benzene ring, are employed, then the process according to the invention can be carried out at a temperature of below 0° C.

Examples of the thionyl halide employed in the process according to the invention are thionyl fluoride, thionyl chloride, thionyl bromide and thionyl iodide, with thionyl chloride being a preferred example.

Thionyl halide is preferably employed in amounts of from 1.0 to 5.0 mol, preferably from 1.5 to 2.5 mol, based on each mole of silane employed.

Examples of the Lewis acids employed in the process according to the invention are titanium tetrachloride, zirconium tetrachloride, tin tetrachloride, silicon tetrachloride, aluminum trichloride, boron trichloride and antimony pentachloride, with titanium, zirconium and tin tetrachlorides being preferred examples.

The Lewis acids can be employed in catalytic amounts. The Lewis acid is preferably employed in amounts of from 0.05 to 1.0 mol, preferably from 0.1 to 0.4 mol, based on each mole of silane employed.

The inert organic solvent employed in the process according to the invention is preferably aprotic and immiscible or only sparingly miscible with water. Examples of aprotic solvents are chlorinated hydrocarbons such as methylene chloride, 1,1,1-trichloroethane and trichloroethylene, and aromatic compounds such as toluene, xylene, ethylbenzene and dimethylformamide.

The inert organic solvent is preferably employed in quantities of from 50 to 500 parts by weight per 100 parts by weight of silane.

In the 1st stage of the process according to the invention the sulfonium salt can be isolated with complex anions of the Lewis acids employed, for example as the hexachlorostannate when tin tetrachloride is used. However, since most of these salts readily eliminate hydrogen halide and are therefore unstable under ambient conditions, it is preferred to add bases and thus destroy completely the complex anion and any excess Lewis acid. The base preferably employed is sodium hydroxide, with further examples of bases being potassium hydroxide and aqueous ammonia.

The base is preferably employed in amounts of from 1.0 to 1.2 mol per mole of halide which can be removed as acid by hydrolysis. Since thionyl chloride is preferably employed in the process according to the invention, a sulfonium chloride is preferentially obtained. The sulfonium halide is recovered from the aqueous phase after separating off the organic phase.

Intermediates during the formation of the sulfonium salts are sulfides and sulfoxides, which may also be contained to a minor extent in the sulfonium salt. Because of their chemical similarity with the sulfonium salt in the case of relatively long-chain radicals D, E and F, separation is quite complex. If the sulfonium salts are obtained as noncrystalline, viscous oils, intermediates which have not fully reacted are preferably left in them. These intermediates are at the same time also decomposition products of the sulfonium salts after UV irradiation, whereby at the end of the reaction sequence acids are formed which initiate cationic polymerizations.

The halide of the sulfonium halides can, in a 2nd process stage, be exchanged for a less nucleophilic anion of a stronger acid.

Examples of $M^+$ are $Na^+$, $K^+$, $Li^+$, $NH_4^+$ and $NR_4^{4+}$ in which $R^4$ is a monovalent hydrocarbon radical having 1 to 8 carbon atoms per radical.

Examples of radicals $R^4$ are alkyl radicals, such as the methyl, ethyl and n-butyl radicals.

Preferred examples of alkali metal salts $M^+Y^-$ are $NaPF_6$, $NaAsF_6$ and $NaSbF_6$, with $NaSbF_6$ being particularly preferred.

The alkali metal salt is preferably employed in amounts of from 1.1 to 1.5 mol, preferably from 1.1 to 1.2 mol, per mole of the sulfonium halide obtained in the 1st stage of the process according to the invention.

Anion exchange is carried out preferably in the presence of an organic solvent. The organic solvent used is preferably one in which the sulfonium halide and the alkali metal salt $M^{+Y-}$ are readily soluble but in which the alkali metal halide $M^{+Z-}$ formed is of poor solubility. Examples of organic solvents are ketones such as acetone, methyl ethyl ketone and methyl isobutyl ketone; esters such as ethyl acetate, butyl acetate and ethyl butyrate, and alcohols such as ethanol, isopropanol and butanol.

The reaction carried out optionally in the 2nd stage is preferably effected by mixing solutions of the sulfonium halide and of the alkali metal salt $M^+Y^-$ in organic solvent. They are mixed preferably at room temperature and at the pressure of the surrounding atmosphere. However, it is also possible to use higher or lower temperatures.

The alkali metal halide formed in the salt exchange, such as sodium chloride, precipitates after the mixing operation and can be filtered off.

If the alkali metal salt, such as sodium hexafluoroantimonate, is employed in a slight excess, more than 95% anion exchange is achieved. A substantially uncontaminated solution of sulfonium hexafluoroantimonate is obtained. Any inorganic salts it contains are removed by evaporating the solution and redissolving the oil in organic solvent, preferably a weakly polar organic solvent such as toluene, cyclohexane or n-alkanes. Refiltration gives uncontaminated solutions of the sulfonium salts. The organic solvent can be removed or the pure sulfonium salts can be left, for better handling, preferably in from 30 to 60% strength solution.

The process according to the invention can be carried out batchwise, semicontinuously or fully continuously.

The sulfonium salts are photosensitive and decompose, for example when irradiated with ultraviolet light, by a multistage mechanism which is described in the book "UV-Curing: Science & Technology" by P. Pappas on page 34. The active end product of this photolysis is considered to be the Brönsted acid formed, e.g. $HPF_6$, $HAsF_6$ or $HSbF_6$, which in turn initiates the polymerization of cationically polymerizable substances such as epoxides or vinyl ethers.

The sulfonium salts according to the invention are suitable as photoinitiators for the polymerization of cationically polymerizable organic substances such as epoxides, vinyl ethers, organopolysiloxanes containing epoxy groups, organopolysiloxanes containing alkenyloxy groups, such as vinyloxy groups or propenyloxy groups, and olefins. Such substances are described, for example, in U.S. Pat. No. 5,057,549, DE-A 40 02 922 and in the patents mentioned at the outset.

EXAMPLE 1 a) 4 mg of platinum in the form of hexachloroplatinic acid are added to 88.5 g (0.66 mol) of allyl phenyl ether under a nitrogen atmosphere and the mixture is heated to 80° C. 125 g of dimethylchlorosilane are metered into the mixture over the course of two hours, the bottom temperature falling to below 50° C. The mixture is stirred for a further six hours under gentle reflux. After fractional distillation, a total of 112 g of 3-phenoxypropyldimethylchlorosilane are obtained. The product has an acid number of 248 (theoretically 244).

b) 0.5 mol of an ethyl Grignard solution in diethyl ether is initially charged under a protective gas atmosphere. At room temperature, 92 g (0.40 mol) of the chlorosilane whose preparation is described above under a) are metered in. The mixture is then heated to boiling and stirred at 40° C. for a further two hours. The magnesium salts are then dissolved by the addition of dilute hydrochloric acid. After phase separation, the ether phase is washed with twice 300 ml of water and concentrated under a slight vacuum and the silane is distilled over at 3 hPa (absolute). 85 g of a colorless, highly fluid liquid are obtained which, according to the $^1H$ NMR spectrum, is pure 3-phenoxypropyldimethylethylsilane. The iodine number (=the number which indicates how many g of iodine are bound by 100 g of substance) is 115.2 (theoretically 114.4).

c) 20.0 g (90 mmol) of 3-phenoxypropyldimethylethylsilane, whose preparation is described above under b), in 30 g of methylene chloride are added dropwise at 0° C to a solution of 20 g of thionyl chloride and 5 g of tin tetrachloride in 30 g of methylene chloride. The mixture is brought to room temperature and stirred for 3 hours. Volatile constituents are removed at 40° C. in vacuo, and the residue is taken up in ethanol. The hexachlorostannate is hydrolyzed by the addition of sodium hydroxide solution until a weakly basic reaction is obtained, and the mixture is filtered and again concentrated at 40° C in vacuo. 15.5 g of a yellow oil are obtained which crystallizes slowly. The $^1H$ NMR spectrum shows the typical pattern of a para- substituted aromatic compound. According to the $^1H$ NMR spectrum, pure tris[4-(3-dimethylethylsilylpropyl) phenyl]sulfonium chloride is obtained. The salt recrystallized from cyclohexane has a melting point of 110° C.

The solubility of the sulfonium chloride in toluene at 25° C. is investigated. The results are summarized in Table 1.

d) In order to exchange the chloride anions for those of hexafluoroantimonate, 7.3 g (10 mmol) of the sulfonium chloride whose preparation is described above under c) are dissolved in 20 ml of methyl ethyl ketone and, while stirring, a solution of 3 g of sodium hexafluoroantimonate in 15 ml of methyl ethyl ketone is added. The precipitate of NaCl is filtered off and the solution is concentrated by evaporation. The sulfonium hexafluoroantimonate is extracted from the crude oil using toluene. After removal of the solvent in vacuo, 8.8 g of tris[4-(3-dimethylethylsilylpropyl)phenyl] sulfonium hexafluoroantimonate are obtained as an orange-yellow oil which slowly crystallizes.

The solubility of the sulfonium hexafluoroantimonate in cyclohexane at 25° C. is investigated. The results are summarized in Table 1.

Comparative Experiment 1 a) tris[4-Octyloxyphenyl]sulfonium chloride is prepared from octyl phenyl ether in analogy to Example 1 c). The salt recrystallized from toluene has a melting point of 95° C. The solubility of this sulfonium chloride in toluene at 25° C. is compared with that of the sulfonium chloride of Example 1 c) according to the invention (the number of atoms in both compounds is the same; in the sulfonium chloride of Example 1 c) one carbon atom is replaced by a silicon atom). The results are summarized in Table 1.

b) By salt exchange of the above sulfonium chloride with sodium hexafluoroantimonate in 2-butanone, filtration and concentration by evaporation a yellow oil is obtained whose structure is confirmed in the $^1H$ NMR spectrum as tris[4-octyloxyphenyl]sulfonium hexafluoroantimonate. It is identical with the product of Example 8 of EP-A 404 031 mentioned at the outset, which in that example is prepared in a multistage synthesis. The solubility of this sulfonium hexafluoroantimonate in cyclohexane is compared with that of the sulfonium hexafluoroantimonate of Example 1 d) according to the invention (the number of atoms in the two compounds is the same; in the sulfonium chloride of Example 1 d) one carbon atom is replaced by a silicon atom). The results are summarized in Table 1.

TABLE 1

| Example or Comparative Experiment | g of Sulfonium salt/100 g of toluene or cyclohexane |
| --- | --- |
| E 1c) Cl⁻ | >100 g/100 g toluene |
| C 1a) Cl⁻ | 60 g/100 g toluene |
| E 1d) SbF$_6$⁻ | 0.36 g/100 g cyclohexane |
| C 1b) SbF$_6$⁻ | <0.10 g/100 g cyclohexane |

The difference in solubility between the sulfonium salts according to the invention and those of EP-A 404 031 is considerable.

EXAMPLE 2 a) 690 g of 2-phenoxyethanol together with 470 g of allyl chloride are added to a solution of 600 g of sodium hydroxide and 14 g of trimethylbenzylammonium chloride in 600 ml of water. The mixture is heated at reflux and is vigorously stirred until the temperature of the gas space has reached about 90° C. After the mixture has been cooled, 1.1 l of water are added and the aqueous phase is separated off after complete dissolution of the salts. It is then washed twice with 300 ml of 10% strength sodium chloride solution. The organic phase is fractionally distilled at 8 hPa (absolute) and 877 g (98.5% of theory) of pure 2-allyloxyethyl phenyl ether are obtained at 73°–76° C.

b) 6 mg of platinum in the form of a solution of the complex with 1,3-divinyltetramethyldisiloxane are added to 290 ml (2.6 mol) of dimethylchlorosilane and the mixture is heated at reflux under a nitrogen atmosphere. 356 g of the 2-allyloxyethyl phenyl ether whose preparation is described above under a) are added dropwise over the course of about 2 hours, the temperature of the mixture being adjusted to 80° C. After 2 hours the reflux comes virtually to an end. The crude product is fractionated in vacuo, the main fraction being taken off at 95°–110° C. (2 hPa). 437 g of 3-(2-phenoxyethoxy)propyldimethylchlorosilane are obtained with an acid number of 207 (theoretically 205). The $^1$H NMR spectrum shows that the product contains neither starting material nor its 1-propeneoxy isomer.

c) 410 g (1.50 mol) of the distilled chlorosilane whose preparation is described above under b) are added dropwise at 70–°80° C. to an octyl Grignard solution in tetrahydrofuran comprising 54 g of magnesium turnings, 305 g of 1-chlorooctane and a total of 1 l of anhydrous tetrahydrofuran. After a further 3 hours at 75° C., most of the tetrahydrofuran is removed by distillation and a solution of 250 g of concentrated hydrochloric acid in 500 ml of water is added dropwise. The crude silane separated off is fractionated in vacuo using a short Vigreux column. 447 g of colorless distillate are obtained which according to the $^1$H NMR spectrum is pure 3-(2-phenoxyethoxy)propyldimethyloctylsilane and has an acid number of less than 1.

d) The procedure of Example 1 under c) is repeated with the modification that 31.5 g (90 mmol) of the silane whose preparation is described above under c) are used instead of the 20.0 g of the silane of Example 1 c), and toluene is used instead of methylene chloride. 27 g of an orange oil are obtained. The $^1$H NMR spectrum shows a number of AA'BB' systems. The main product is tris[4-(2-(3-dimethyloctylsilylpropyloxy)ethoxy)phenyl] sulfonium chloride, at approximately 65 mol %. By-products included are the corresponding sulfide and sulfoxide intermediates. The sulfonium salt is soluble in both n-heptane and hexamethyldisiloxane over the entire concentration range from 1–75%, with no exceptions.

e) The procedure of Example 1 under d) is repeated with the modification that 17.2 g (10 mmol) of the sulfonium chloride whose preparation is described above under d) are used instead of the 7.3 g of the sulfonium chloride of Example 1 d). The sulfonium hexafluoroantimonate is extracted from the crude oil using cyclohexane, and the extract is then filtered and concentrated by evaporation at 40° C. in vacuo. The $^1$H NMR spectrum of the resulting tris[4-(2-(3-dimethyloctylsilylpropyloxy)ethoxy)phenyl] sulfonium hexafluoroantimonate shows complete conversion of the sulfonium chloride. The signals of the protons ortho to the sulfur are displaced upfield by 0.2 ppm.

EXAMPLE 3 a) 148 g (1.0 mol) of 2-allylanisole are mixed with 8 mg of hexachloroplatinic acid under a nitrogen atmosphere and heated to 70° C. 114 g (1.2 mol) of dimethylchlorosilane are metered into the mixture over the course of two hours and the mixture is stirred at 70° C. for a further four hours. Excess dimethylchlorosilane is then removed in vacuo and 2-propenylanisole which is formed by isomerization is separated off using a short Vigreux column. 204 g of 3-(2-anisyl)propyldimethylchlorosilane are obtained as a clear liquid having an acid number of 227.

b) For alkylation, 122 g (0.50 mol) of the chlorosilane whose preparation is described above under a) are added dropwise to 320 ml of a 1.8 molar solution of n-octylmagnesium chloride in tetrahydrofuran and the mixture is stirred at reflux temperature for a further six hours. The mixture is then admixed with sufficient dilute hydrochloric acid for two clear phases to form. After separation of the magnesium salt solution, the remaining mixture is washed three times with 200 ml of water and the residual tetrahydrofuran is removed. After distillation in vacuo, 144 g of 3-(2-anisyl)propyldimethyloctylsilane are obtained having an iodine number of 80.1 and an acid number of less than 1. The $^1$H NMR spectrum shows a ratio of methoxy to n-octyl groups of exactly 1.0.

c) The procedure of Example 1 under c) is repeated with the modification that 29.0 g (90 mmol) of the 3-(2-anisyl)propyldimethyloctyl silane whose preparation is described above under b) are employed instead of the 20 g of the silane of Example 1 c) and the crude salt is extracted in cyclohexane instead of ethanol. After removal of the solvent, 27.7 g of a yellowish oil are obtained whose H NMR spectrum reveals a content of more than 90% of the corresponding sulfonium chloride. The aromatic proton signals correspond to 1,2,4-substitution. The tris[3-(3-dimethyloctylsilylpropyl)-4-methoxyphenyl]sulfonium salt is of unlimited solubility in both n-heptane and hexamethyldisiloxane.

d) The procedure of Example 2 under e) is repeated with the modification that 11.0 g (10 mmol) of the sulfonium chloride whose preparation is described above under c) are employed instead of the 17.2 g of the sulfonium chloride of Example 2 e). The concentrated product (12.2 g) crystallizes slowly on standing at room temperature. According to the $^1$H NMR spectrum, pure tris[3-(3-dimethyloctylsilylpropyl)-4-methoxyphenyl]sulfonium hexafluoroantimonate is obtained. A sample recrystallized from hexamethyldisiloxane has a melting point of 67° C.

EXAMPLE 4 a) 600 g of sodium hydroxide are dissolved in 600 ml of water, and 14 g of trimethylbenzylammoniumchloride and 670 g of 2-allylphenol are added. The mixture is heated to about 80° C. and a total of 1030 g of 1-bromobutane are added dropwise over the course of about 2 hours. After the internal temperature has risen to almost 100° C., reaction is allowed to continue at the same temperature for a further 4 hours. The resulting salt is dissolved by addition of 1250 ml of water and the ether is taken up in 500 ml of toluene. The organic phase is separated off and washed twice with 500 ml of 5% strength NaOH and is concentrated at 50° C. and 5 hPa. 921 g of crude 2-butoxyallylbenzene, containing traces of solvents (toluene, n-butanol), and small quantities of ring-alkylated 2-butoxyallylbenzene are obtained. According to the $^1$H NMR spectrum the O-alkylation is complete.

b) 921 g of approximately 94% pure 2-butoxyallylbenzene, whose preparation is described above under a), are charged together with 15 mg of platinum as the complex with 1,3-divinyltetramethyldisiloxane and heated at 80° C. under a nitrogen atmosphere. A total of 620 g of dimethylchlorosilane are added dropwise over the course of 5 hours. Reaction is allowed to continue for a further 2 hours at about 70° C. and excess silane is distilled off. Distillation under an oil pump vacuum yields between 95 and 115° C. a total of 1135 g of colorless 3-(2-butoxyphenyl)propyldimethylchlorosilane having an acid number of 203 (theoretically 198).

c) A total of 275 g of the chlorosilane of acid number 203 whose preparation is described above under b) are added dropwise to an octyl Grignard solution comprising 1.50 mol of magnesium and 1.55 mol of 1-chlorooctane in 700 ml of tetrahydrofuran, at 70° C., and the milky reaction mixture is stirred at the same temperature overnight. Tetrahydrofuran is then substantially removed by distillation, and the magnesium salts are dissolved with dilute hydrochloric acid. The organic phase is separated off, filtered and freed from volatile substances in vacuo at 100° C. 347 g of 3-(2-butoxyphenyl)propyldimethyloctylsilane are obtained. The $^1$H NMR spectrum shows a ratio of butoxy to octyl groups of exactly 1.0.

d) The procedure of Example 1 under c) is repeated with the modification that 326 g of the silane whose preparation is described above under c) are employed instead of the 20.0 g of the silane of Example 1 c). Working up gives 340 g of a highly viscous yellowish oil whose $^1$H NMR spectrum shows the complete conversion of the silane employed and the typical pattern of a 1,2,4-substituted aromatic compound. tris[3-(3-Dimethyloctylsilylpropyl)- 4-butoxyphenyl]sulfonium chloride is of unlimited solubility in hexamethyldisiloxane.

e) 115 g of the sulfonium chloride whose preparation is described above under d) are diluted with 150 g of methyl ethyl ketone, and a solution of 31 g of NaSbF$_6$ in 150 g of methyl ethyl ketone is added. After about one hour, the NaCl is filtered off, the methyl ethyl ketone is removed in vacuo, the turbid oil is dissolved with 300 ml of cyclohexane and the solution is filtered. After the solvent has been evaporated in vacuo, 130 g of a yellowish oil are obtained whose $^1$H NMR spectrum reveals complete salt exchange to give the hexafluoroantimonate. The salt can be dissolved as desired in n-heptane.

f) Similarly, 115 g of the sulfonium chloride whose preparation is described above under d) are reacted with 17 g of NaPF$_6$ in 150 g of ethanol and worked up as described above under e). 123 g of tris[3-(3-dimethyloctylsilylpropyl)-4-butoxyphenyl]sulfonium hexafluorophosphate are obtained as a viscous orange-yellow oil which crystallizes slowly and whose $^1$H NMR spectrum shows the same signal pattern as that of Example 4 e). It can be dissolved as desired in n-heptane.

What is claimed is:

1. A sulfonium salt of the general formula

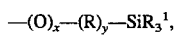

in which each A is identical or different and is a monovalent radical of the general formula

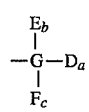

in which

G is an aromatic hydrocarbon radical having 6 to 14 carbon atoms per radical or is an aromatic hydrocarbon radical having 5 to 14 ring atoms per radical which contains at least one oxygen and/or sulfur atom, with the proviso that one hydrogen atom in the radical G is replaced by a chemical bond to the sulfur atom, and D, E and F are each substituents of G, where D is a radical of the formula $$-(O)_x-(R)_y-SiR_3^1,$$

E is a radical of the formula $$-OR^2,$$

F is a radical of the formula $$-R^3,$$

a is 1, 2 or 3, b is 0, 1 or 2, c is 0, 1 or 2, x is 0 or 1, y is 0 or 1,

R is a divalent hydrocarbon radical having 1 to 18 carbon atoms per radical, which is optionally interrupted by at least one oxygen atom and/or one sulfur atom and/or one carboxyl group, R$^1$ is identical or different and is a monovalent hydrocarbon radical having 1 to 18 carbon atoms per radical, which is optionally interrupted by at least one oxygen atom, R$^2$ is a monovalent hydrocarbon radical having 1 to 18 carbon atoms per radical, which is optionally interrupted by an leash one oxygen atom, R$^3$ is a monovalent hydrocarbon radical having 1 to 10 carbon atoms per radical, which is optionally interrupted by at least one oxygen atom and/or one sulfur atom, and X$^-$ is a halide ion Z$^-$, a tosylate anion or a weakly nucleophilic or non-nucleophilic anion Y$^-$ selected from the group consisting of CF$_3$CO$_2^-$, BF$_4^-$, PF$_6^-$, AsF$_6^-$, SbF$_6^-$, ClO$_4^-$, HSO$_4^-$ and F$_{(2n+1-m)}$H$_m$—SO$_3^-$, in which n is an integer from 1 to 12 and m is 0 or an integer of up to 2n−1.

2. A sulfonium said as claimed in claim 1, wherein A is a radical of the formula

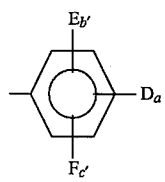

in which D, E and F are each a radical bonded in the 2-, 3-, 4-, 5- or 6-position to the benzene ring, D is a radical of the formula $$-(O)_x-(R)_y-SiR_3^1$$

E is a radical of the formula $$-OR^2,$$

F is a radical of the formula $$-R^3,$$

R is a divalent hydrocarbon radical having 1 to 18 carbon atoms per radical, which is optionally interrupted by at least one oxygen atom and/or one sulfur atom and/or one carboxyl group, each R$^1$ is identical or different and is a monovalent hydrocarbon radical having 1 to 18 carbon atoms per radical which is optionally interrupted by at least one oxygen atom, $R^2$ is a monovalent hydrocarbon radical having 1 to 18 carbon atoms per radical, which is optionally interrupted by at least one oxygen atom, $R^3$ is a monovalent hydrocarbon radical having 1 to 10 carbon atoms per radical which is optionally interrupted by at least one oxygen atom and/or one sulfur atom, a is 1, 2 or 3, b' is 0 or 1, c' is 0 or 1, x is 0 or 1 and y is 0 or 1.

3. A sulfonium salt as claimed in claim 1, having the general formula

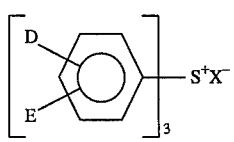

in which D is a radical of the formula $$-(O)_x-(R)_y-SiR^1{}_3,$$

and E is a radical of the formula $$-OR^2$$

in which

R is a divalent hydrocarbon radical having 1 to 18 carbon atoms per radical, which is optionally interrupted by at least one oxygen atom and/or one sulfur atom and/or one carboxyl group, $R^1$ is identical or different and is a monovalent hydrocarbon radical having 1 to 18 carbon atoms per radical, which is optionally interrupted by at least one oxygen atom, $R^2$ is a monovalent hydrocarbon radical having 1 to 18 carbon atoms per radical, which is optionally interrupted by at least one oxygen atom, $X^-$ is a halide ion $Z^-$, a tosylate anion or a weakly nucleophilic or non-nucleophilic anion $Y^-$ selected from the group consisting of $CF_3CO_2^-$, $BF_4^-$, $PF_6^-$, $AsF_6^-$, $SbF_6^-$, $ClO_4^-$, $HSO_4^-$ and $C_nF_{(2n+1-m)}H_m$—$SO_3^-$, in which n is an integer from 1 to 12 and m is 0 or an integer of up to 2n–1, x is 0 or 1 and y is 0 or 1.

4. A sulfonium salt as claimed in claim 3, having the formula

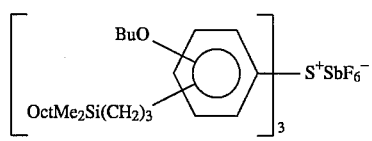

in which Me is a methyl radical and Oct is an n-octyl radical.

5. A process for the preparation of a sulfonium salt as claimed in claim 1, which comprises in a 1st stage reacting a silane of the formula

in which

G' is an aromatic hydrocarbon radical having 6 to 14 carbon atoms per radical or an aromatic hydrocarbon radical having 5 to 14 ring atoms per radical and containing at least one oxygen and/or sulfur atom, and D, E and F are each substituents of G' where D is a radical of the formula $$-(O)_x-(R)_y-SiR^1{}_3,$$

and E is a radical of the formula $$-OR^2,$$

F is a radical of the formula $$-R^3,$$

a is 1, 2 or 3, b is 0, 1 or 2, c is 0, 1 or 2, x is 0 or 1, y is 0 or 1,

R is a divalent hydrocarbon radical having 1 to 18 carbon atoms per radical, which is optionally interrupted by at least one oxygen atom and/or one sulfur atom and/or one carboxyl group, $R^1$ is identical or different and is a monovalent hydrocarbon radical having 1 to 18 carbon atoms per radical, which is optionally interrupted by at least one oxygen atom, $R^2$ is a monovalent hydrocarbon radical having 1 to 18 carbon atoms per radical which is optionally interrupted by at least one oxygen atom, and $R^3$ is a monovalent hydrocarbon radical having 1 to 10 carbon atoms per radical, which is optionally interrupted by at least one oxygen atom and/or a sulfur atom, with thionyl halide in the presence of a Lewis acid and an inert organic solvent to give a sulfonium halide of the formula

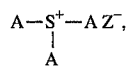

in which each A is identical or different and is a monovalent radical of the general formula

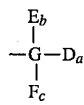

in which

G is an aromatic hydrocarbon radical having 6 to 14 carbon atoms per radical or an aromatic hydrocarbon radical having 5 to 14 ring atoms per radical and containing at least one oxygen and/or sulfur atom, with the proviso that one hydrogen atom in the radical G is replaced by a chemical bond to the sulfur atom and D, E and F are each substituents of G, D, E, F, a. b and c are as defined above and $Z^-$ 1 is a halide ion, and optionally in a 2nd stage reacting the resulting sulfonium halide with an alkali metal salt of the formula $$M^+Y^-,$$

in which $M^+$ is an alkali metal cation, ammonium ion or a quaternary ammonium cation, $Y^-$ is a weakly nucleophilic or non-nucleophilic anion selected from the group consisting of $CF_3CO_2^-$, $BF_4^-$, $PF_6^-$, $AsF_6^-$, $SbF_6^-$, $ClO_4^-$, $HSO_4^-$ and $C_nF_{(2n+1-m)}H_m\text{—}SO_3^-$, in which n is an integer from 1 to 12 and m is 0 or an integer of up to 2n−1, in the presence of organic solvent.

6. The process as claimed in claim 5, wherein $Y^-$ is an anion of the formula $SbF_6^-$.

* * * * *

UNITED STATES PATENT AND TRADEMARK OFFICE
CERTIFICATE OF CORRECTION

PATENT NO. : 5,466,845
DATED : November 14, 1995
INVENTOR(S) : Christian Herzig

It is certified that error appears in the above-indentified patent and that said Letters Patent is hereby corrected as shown below:

Claim 1, column 14, line 35, after "and" delete "$F(2n+1-m)$" and insert in lieu of --- $C_nF(2n+1-m)$ ---.

Claim 2, column 14, line 67, at the beginning of the line, delete "each".

Claim 5, column 17, line 4, after "Z-" delete "1"; column 18, line 3, after "and" delete "$C_nF(2-$" and insert at the beginning of line 4 --- $C_nF(2$ ---.

Signed and Sealed this

Fifth Day of March, 1996

Attest:

BRUCE LEHMAN

Attesting Officer    Commissioner of Patents and Trademarks